(12) United States Patent
Ash et al.

(10) Patent No.: US 7,374,951 B2
(45) Date of Patent: May 20, 2008

(54) SYSTEM AND APPARATUS FOR USE IN DETECTING MICROORGANISMS

(75) Inventors: Megan Ash, New South Wales (AU); David William Edwards, New South Wales (AU); Aaron Peter Gibbeson, New South Wales (AU); Dianne Barbara Kerr, New South Wales (AU); Lisa Frances Moncur, New South Wales (AU); Philip Albert Myers, New South Wales (AU)

(73) Assignee: TECRAInternational Pty Ltd., New South Wales (AU)

( * ) Notice: Subject to any disclaimer, the term of this patent is extended or adjusted under 35 U.S.C. 154(b) by 582 days.

(21) Appl. No.: 10/492,188

(22) PCT Filed: Oct. 7, 2002

(86) PCT No.: PCT/AU02/01362

§ 371 (c)(1),
(2), (4) Date: Sep. 15, 2004

(87) PCT Pub. No.: WO03/031980

PCT Pub. Date: Apr. 17, 2003

(65) Prior Publication Data

US 2005/0032037 A1 Feb. 10, 2005

(30) Foreign Application Priority Data

Oct. 10, 2001 (AU) .................................... PR8192
Jun. 26, 2002 (AU) .................................... PS3201

(51) Int. Cl.
*G01N 33/53* (2006.01)

(52) U.S. Cl. .................. 436/518; 436/514; 436/169; 436/172; 436/175; 436/807; 435/287.7; 435/287.8; 435/287.9; 435/805; 422/56; 422/58; 422/59; 422/60

(58) Field of Classification Search ................ 436/514, 436/518, 169, 172, 175, 807, 287.7; 435/287.8, 435/287.9, 805; 422/56–60
See application file for complete search history.

(56) References Cited

U.S. PATENT DOCUMENTS 4,225,575 A  9/1980 Piasio et al.

(Continued)

FOREIGN PATENT DOCUMENTS

AU  B-21278/88  3/1989

(Continued)

OTHER PUBLICATIONS

Hughes, D. et al; "TECRA® Unique™ Test for Rapid Detection of *Salmonella* in Food: Collaborative Study"; *Journal of AOAC International*; vol. 84, No. 2, pp. 416-429 (2001).

(Continued)

*Primary Examiner*—Bao-Thuy L. Nguyen
(74) *Attorney, Agent, or Firm*—Nixon & Vanderhye

(57) ABSTRACT

A system and an apparatus for use in detecting a target microorganism or agent is disclosed which involves a solid support carrying a binding partner specific for the particular microorganism or agent and the solid support being characterised in that it defines means for protecting the binding partner from being dislodged or scraped off the solid support by physical means. The provision of protection against the binding partner being dislodged from or scraped off the solid support improves the reliability of tests such as immunoassays being conducted with the solid support and also enables such tests to be automated. Modules and machines for use with the solid support, and the automated conduct of tests ate also disclosed.

12 Claims, 6 Drawing Sheets

U.S. PATENT DOCUMENTS

Figure 8A:
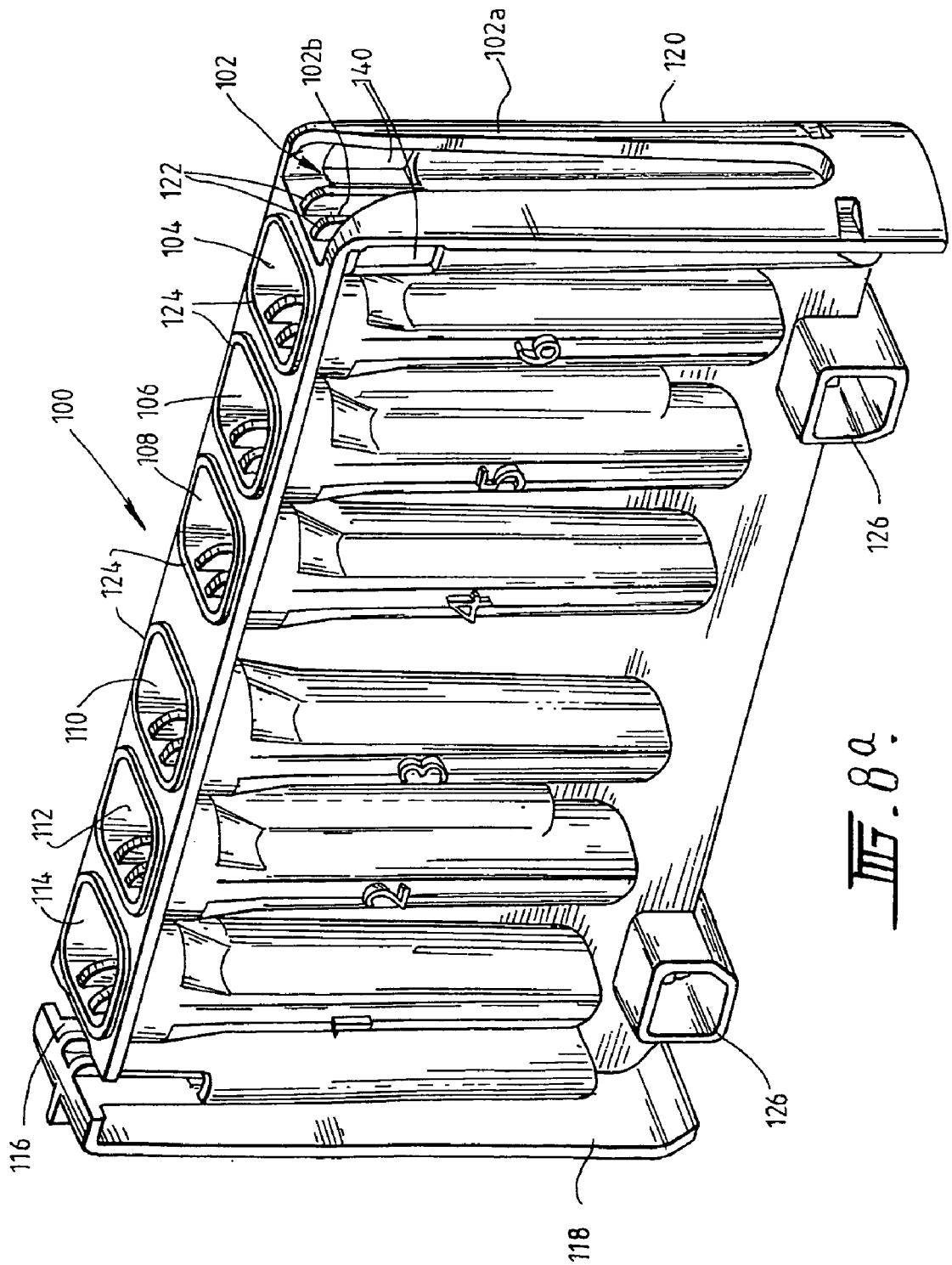

| | | | |
|---|---|---|---|
| 4,452,679 A | | 6/1984 | Dunn et al. |
| 4,803,170 A | * | 2/1989 | Stanton et al. ............... 436/518 |
| 4,938,927 A | * | 7/1990 | Kelton et al. .................. 422/64 |
| 4,985,206 A | * | 1/1991 | Bowman et al. ............... 422/99 |
| RE34,864 E | | 2/1995 | Batz et al. |
| 6,004,766 A | | 12/1999 | Atrache et al. |
| 6,303,389 B1 | * | 10/2001 | Levin et al. ................. 436/518 |
| 6,844,200 B2 | * | 1/2005 | Brock ......................... 436/514 |
| 6,855,561 B2 | * | 2/2005 | Jerome et al. ............... 436/514 |
| 2002/0150501 A1 | * | 10/2002 | Robertson et al. ............ 422/56 |

FOREIGN PATENT DOCUMENTS

| | | |
|---|---|---|
| EP | 0 194 789 | 9/1986 |
| EP | 0 194 789 A2 | 9/1986 |
| WO | WO 91/16377 | 10/1991 |
| WO | WO 91/19003 | 12/1991 |
| WO | WO 95/06256 | 3/1995 |

OTHER PUBLICATIONS

Kerr, D., et al; "Evaluation of a 22 hour *Salmonella* screening method for foods"; *Journal of Applied Bacteriology*; vol. 77, No. 1, Suppl., p. XV; 1994 (XP002373735).

Meyers, P.A., et al; "A new automated immunoassay system for the detection of foodborne pathogens"; *Journal of Applied Bactgeriology*; vol. 77, No. 1 Suppl., p. XV, 1994 (XP009063985).

Hughes, D., et al; "TECRA® Unique™ Test for Rapid Detection of *Salmonella* in Food: Collaborative Study"; *Journal of AOAC International*; vol. 84, No. 2, pp. 416-429, 2001 (XP002979821).

* cited by examiner

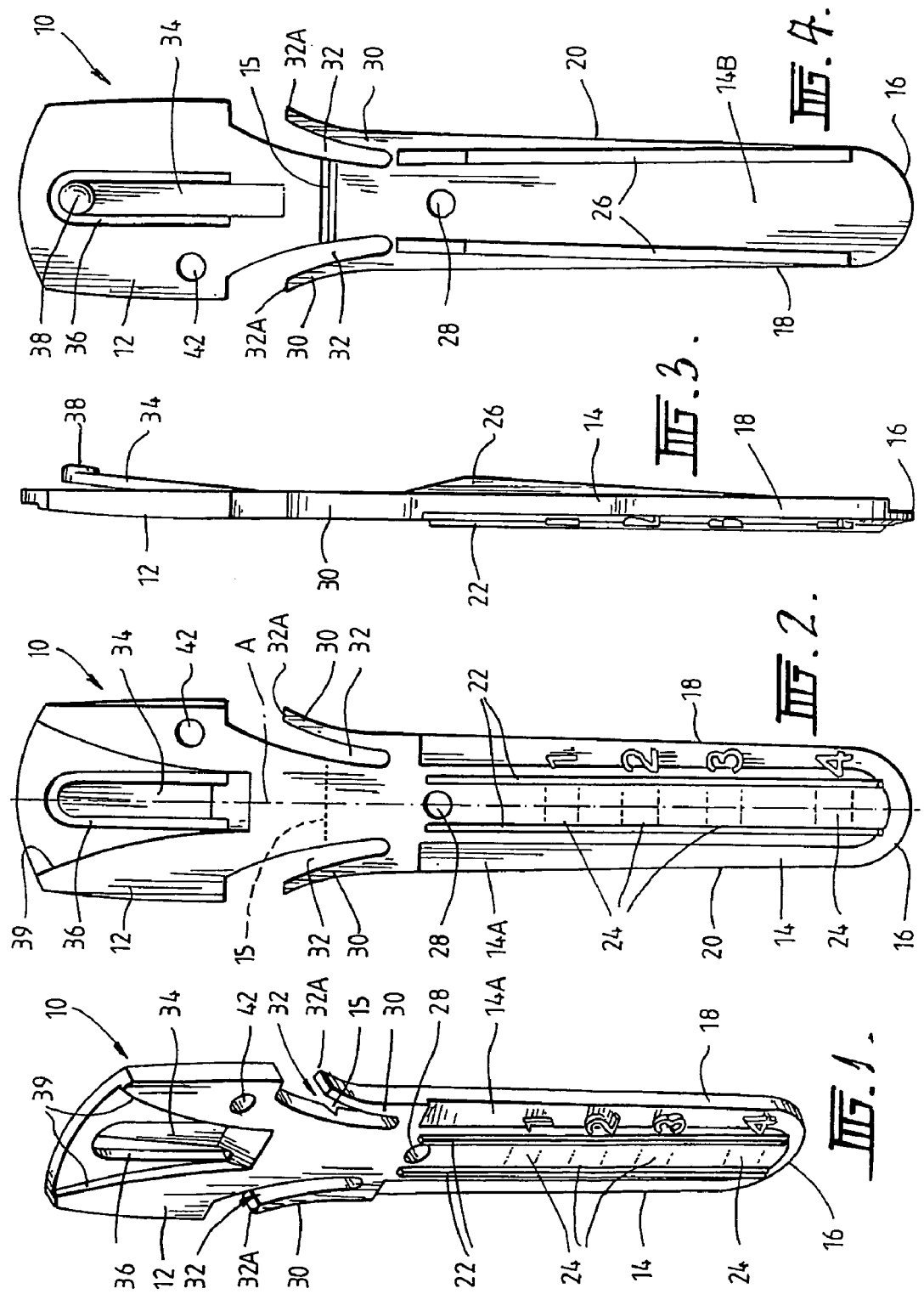

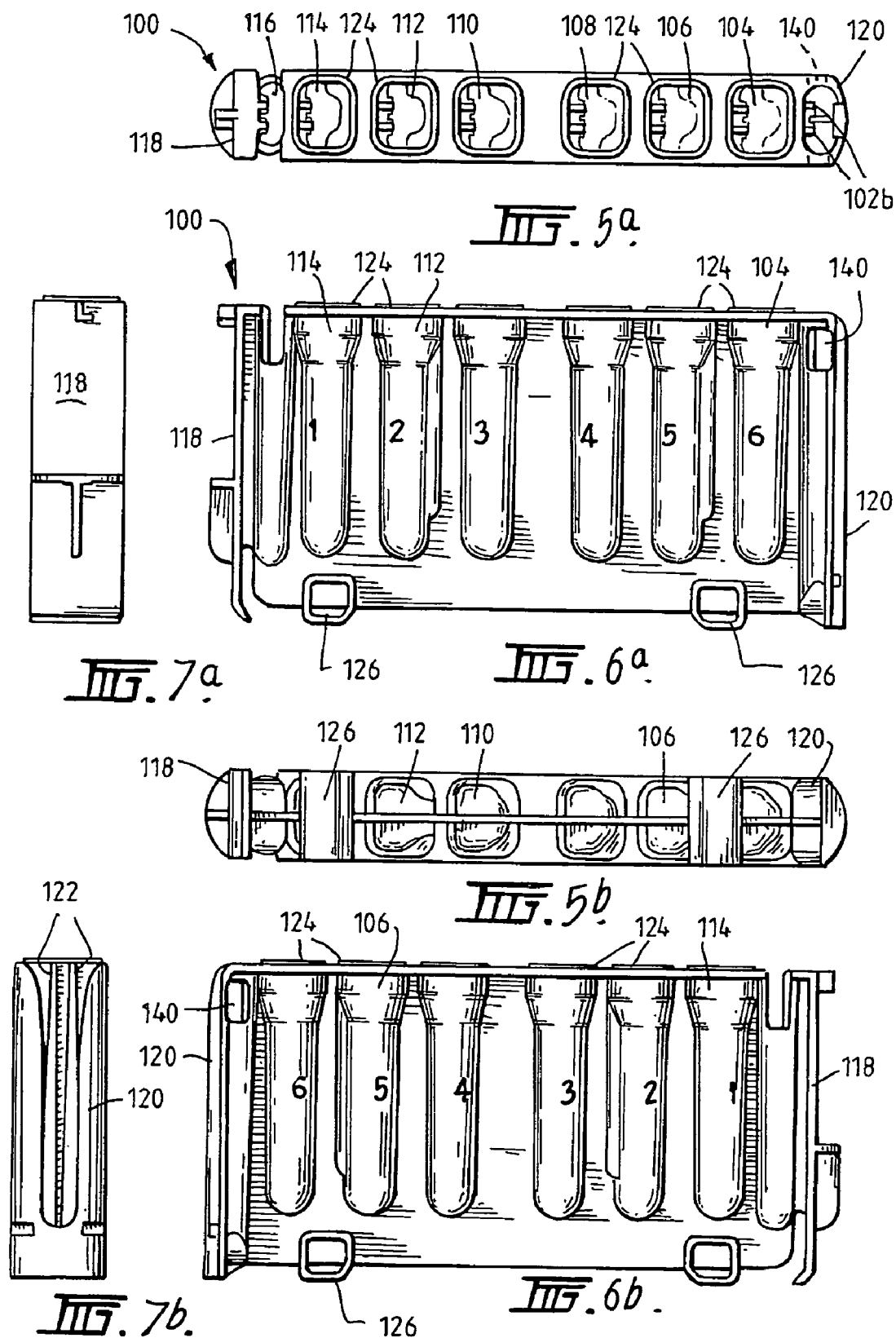

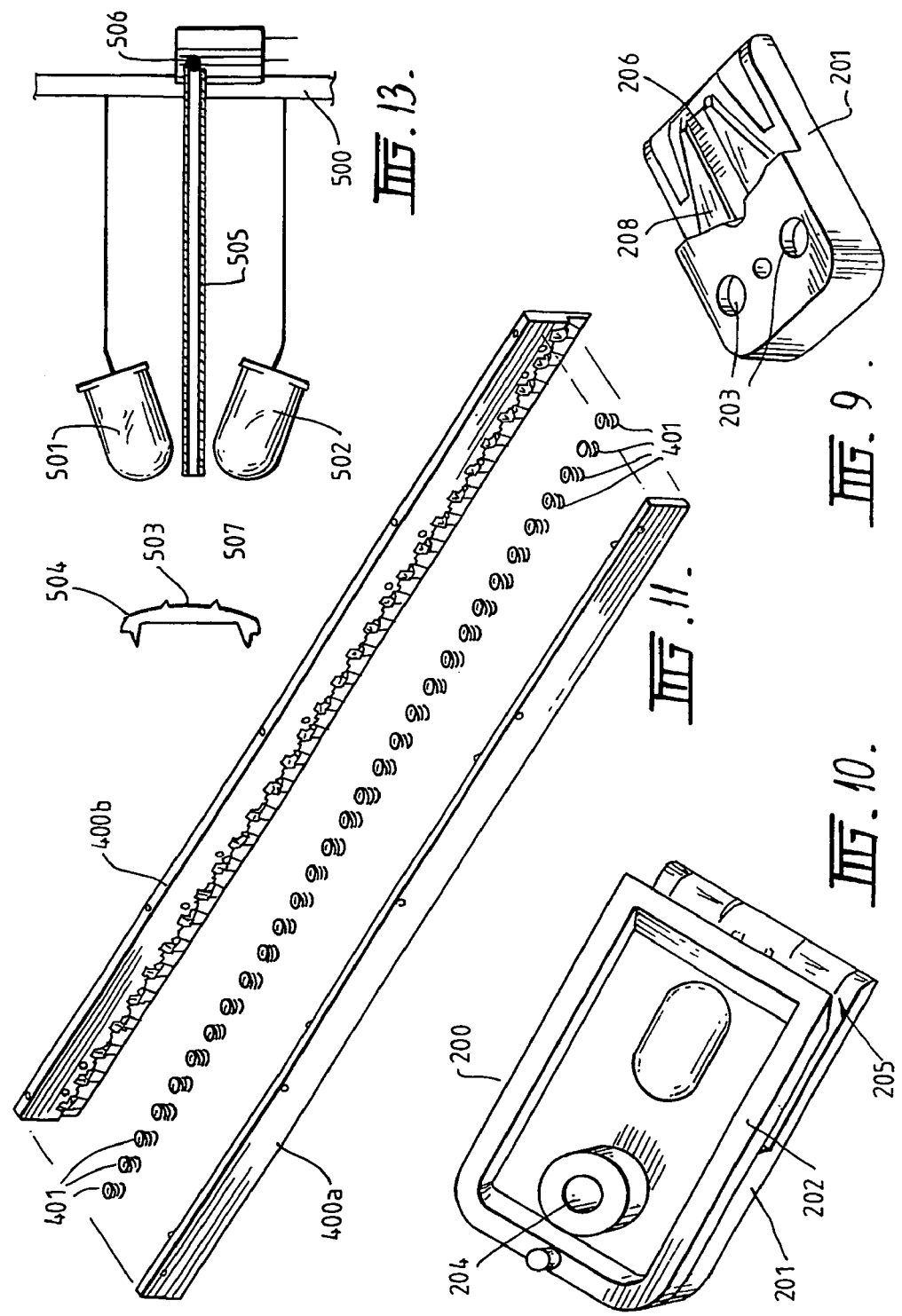

SYSTEM AND APPARATUS FOR USE IN DETECTING MICROORGANISMS

This application is the U.S. National Phase of International Application PCT/AU02/01362 filed 7 Oct. 2002, which designated the U.S.

FIELD OF THE INVENTION

This invention relates to a system and an apparatus for use in detecting a target microorganism or agent. In one particular application of the invention, the system and apparatus is used for the detection of low levels of a target microorganism (eg *Salmonella*) in the presence of competing microorganisms.

BACKGROUND OF THE INVENTION

In the past few years, there has been a worldwide upsurge in the number of reported outbreaks of food poisoning, often caused by *Salmonella* although other bacteria such as *Listeria* have also been responsible for some outbreaks. *Listeria* or *Salmonella* can be found as contaminants in a wide variety of foods, particularly meat products; poultry; egg products; cheese, milk, icecream, and other dairy products; frozen and processed seafood; confectionary; and even vegetables and fruit. *Listeria* and *Salmonella* are recognised by food safety regulators in most countries of the world as being significant contaminants of food and many government food safety regulators require environmental and end product testing for these bacteria, in the food industry. Consequently, it is common practice in the food industry to regularly check for contamination by microorganisms of both food products and food processing environments, such as *Listeria* and *Salmonella*. Similarly, testing for microorganisms is also carried out in other industries such as pharmaceutical and cosmetics manufacturing.

Testing for microorganisms, generally involves taking a food sample (eg 25 g portion) or a swab from the area being tested (nb samples may also be taken from floor sweepings, waste water and filtered air), transferring the sample to a pre-enrichment or enrichment medium in which any injured microorganisms will resuscitate, followed by one or two additional selective enrichment steps to increase the numbers of the microorganisms of interest, and subsequent testing for the presence of the particular microorganisms in the medium using traditional cultural methods or rapid methods such as immunoassays.

There are a number of known rapid methods for testing for *Salmonella*, *Listeria* and other pathogens, some of which are supplied by Tecra® International Pty Ltd of Frenchs Forest, New South Wales, Australia. In one known Tecra® system, also described in Australian patent specification No. 610925, a sample may be tested for, for example, *Salmonella* contamination by a method involving, firstly, transferring the sample to a pre-enrichment medium for sixteen hours. A small aliquot of the pre-enrichment medium is then transferred to a first tube and a dipstick which is coated with antibodies specific for *Salmonella*, is inserted into the first tube to capture any *Salmonella* microorganisms present. After capture, which takes approximately twenty minutes, the dipstick is then washed in a second tube to remove any extraneous material. The dipstick is then transferred to a third tube which includes a growth medium and any *Salmonella* which have attached to the dipstick multiply on the surface of the dipstick until they are present in sufficient numbers for detection. For *Salmonella*, this replication stage typically takes about four hours and after the four hour replication period is over (different periods apply for different microorganisms and different sample types), the dipstick is then transferred to a fourth tube which contains enzyme-linked antibodies specific for *Salmonella* which bind to any *Salmonella* on the dipstick. The dipstick remains in the fourth tube for approximately thirty minutes. The dipstick is then transferred to a fifth tube for washing to remove excess or unbound enzyme-linked antibodies. The dipstick is then transferred to a sixth tube which contains substrate for the enzyme. If *Salmonella* are present, a purple colour is produced on the lower half of the dipstick. A white band across the top of the dipstick acts as a negative control. The dipstick also incorporates a positive (purple coloured) control as confirmation that the test has been carried out correctly.

Similar procedures to that described may be used for testing for *Listeria* and for other selected microorganisms, although the pre-enrichment and growth media, incubation periods, incubation temperature, number and timing of the various stages may vary from microorganism to microorganism.

Although the abovementioned test works well, the test involves numerous steps that require a laboratory technician to monitor and time the procedure and transfer the dipstick, to correct tubes, for the correct period, at the correct times, and at the correct incubation temperature, to ensure that the test is carried out properly.

The foregoing description of prior art, is not to be taken as an admission that the art described forms part of the common general knowledge of the person skilled in the art in Australia or elsewhere.

It is an object of the present invention to provide an improved system and apparatus for detection of target microorganisms (eg bacteria such as *Salmonella* and *Listeria*, and protozoa such as *Cryptosporidium*) and/or agents (eg viruses, prions, toxins, and other analytes including antibodies, antigens, nucleic acids, chemical residues, microbial metabolites and vitamins).

SUMMARY OF THE INVENTION

In a first aspect of the present invention, there is provided a solid support for use in a process for the detection of a particular target microorganism or agent and wherein the solid support carries a binding partner specific for the particular microorganism or agent, the binding partner being capable of selective capture and immobilisation of the microorganism or agent characterised in that the solid support defines means for protecting the binding partner from being dislodged or scraped off the solid support by physical means.

In a preferred embodiment, the solid support is in the form of a dipstick having a generally planar shape defining a longitudinal axis.

The dipstick may define a front face and a rear face. Typically the means for protecting the binding partner from being dislodged from the dipstick includes at least one rail raised from the front face, and extending generally parallel to the longitudinal axis. More preferably, the means for protecting the binding partner from being dislodged from the dipstick includes a pair of such rails, in between which the front face provides an array of regions, typically three or four, spaced apart along the longitudinal axis. Typically, one of those regions will comprise said binding partner, with two of the other regions providing positive and negative controls.

The provision of protection against the binding partner being dislodged from or scraped off the dipstick not only improves the reliability of the test, but also is a significant factor in allowing the process to be automated. If the process of transferring the dipstick from tube to tube when carrying out the testing process is carried out by a machine, the risk of the dipstick brushing against the sides of one or more of the test tubes is increased. If the rails were not present, such contact could scrape the binding partner off the dipstick and potentially compromise the test.

In the preferred embodiment, the binding partners are simply applied to specific regions on the dipstick which are preferably identified by numbers or other suitable indicia.

However, in an alternative embodiment, the array of regions may be defined by recesses in the front face of the dipstick. During the manufacture of the dipstick, the recesses may assist in locating and retaining droplets containing the binding partner (and substances providing the positive control) on the dipstick.

It is preferred that the rear face of the dipstick defines a pair of ribs which extend from the base of the dipstick towards the top of the dipstick and protrude from the rear face and increase in height relative to the rear face as they extend towards the top of the dipstick.

The dipstick may define a lower portion for insertion into a well, tube or the like, and an upper or handle portion to be grasped for moving the dipstick. Both upper and lower portions may define a through hole for checking the location of the dipstick during the process of applying the binding partner to the dipstick, and/or for locating the dipstick for reading results.

The dipstick may also define two flexible outwardly extending arms projecting from opposite sides of the upper part of the lower portion of the dipstick.

Typically, the dipstick will be made out of a plastic which is resistant to gamma radiation to enable sterilisation of the surfaces of the dipstick in accordance with routine methods well known in the art. Preferably, the dipstick is made out of a polystyrene plastic. To assist in the reading of results, the dipstick is preferably of a substantially uniform white colour and has a substantially uniform level of opacity.

The binding partner (and/or substances providing positive and negative controls) may be adhered to the dipstick surface in a number of ways including hydrogen bonding and/or Van der Waals forces or by covalent bonds either directly or through a linker molecule. For example, the binding partner may be conjugated to a biotin molecule and adhered to the dipstick surface via an avidin or streptavidin linker molecule.

The binding partner may be any molecule or substance which specifically binds to the target microorganism or agent. For example, for detection of a target microorganism or a target protein or peptide, the binding partner is preferably selected from antibodies and antibody fragments (eg Fab and scFv fragments) which specifically bind to the target microorganism or target protein or peptide. For a target protein or peptide, the binding partner may also be a receptor molecule to which the target protein or peptide specifically binds. For detection of antibodies, the binding partner may be an antigen or antigenic determinant for the target antibodies. For the detection of a nucleic acid (eg DNA or RNA), the binding partner may be selected from nucleic acids having a complementary nucleotide sequence such that the binding partner specifically hybridises to the target nucleic acid, preferably under conditions of high stringency. A nucleic acid binding molecule may be adhered to the dipstick surface via, for example, a poly-dA probe.

In a particularly preferred embodiment, the dipstick is for use in a process for the detection of a particular target microorganism, and the binding partner is an antibody specific for the particular microorganism wherein the binding partner is capable of selective capture and immobilisation of the microorganism without compromising the ability of the microorganism to replicate.

A module is provided for use with the dipstick. The module defines a starting or "launch" slot for the dipstick, an end or "reading" slot and a series of wells or tubes therebetween. The shape and configuration of the module relative to the dipstick provides a number of key features and advantages.

It is preferred that the two opposed ends of the module have different configurations. For carrying out a plurality of tests in parallel, a tray may be provided on which a plurality of modules may be mounted and secured in side by side relation. One end of the tray defines a first series of formations adapted to mate with only one of the ends of the module, the other end of the tray defines a second series of formations adapted to mate with the other of the ends of the module. This prevents any module being oriented "back to front" on the tray.

In a second aspect of the present invention, there is provided a module for use with the solid support of the present invention comprising a start slot, an end slot and a series of wells or tubes disposed between the start slot and the end slot characterised in that at least the start slot defines a means to ensure that the solid support of the present invention can be inserted into the start slot in one orientation only.

Typically, the start slot, end slot and the wells are sized and configured, defining formations which interact with formations defined on the dipstick such that the dipstick may only be fully inserted in the start slot, end slot and the wells in one orientation only. The means for ensuring that the solid support can only be inserted in one orientation may include a pair of ribs which are spaced apart at approximately the same distance as the rails of the dipstick. The ribs are preferably more closely spaced than the protruding ribs defined on the rear face of the dipstick. Preferably, the width of the slots is greater than the thickness of the dipstick but the width of the slots plus the ribs defined in the slots is less than the thickness of the dipstick. Each of the wells defines a bulge or bulbous which is arranged to face the reactive side of the dipstick in which the recesses are located but which is narrower than the dipstick.

It is preferred that the end slot of the module is configured such that when the dipstick is inserted into that slot, the dipstick locks in place and cannot be easily removed. This ensures that the dipsticks cannot be deliberately or accidentally reused. The means may include cut-out portions in the slot into which the flexible outwardly extending arms of the dipstick snap-fit.

The end slot of the module is also preferably provided with a window through which the results obtained with the dipstick may be read either manually (ie by eye) or through automated means.

It is also preferred that the dipstick be provided with a frangible portion to allow the upper portion of the dipstick to be "snapped" off. Removal of the upper portion of the dipstick when located in the end slot of the module allows for the wells to be readily sealed with, for example, a strip of adhesive-backed foil or tape, for subsequent disposal or for further assessment of the sample. That is, where the test achieves a positive result for the presence of, for example, *Salmonella*, it may be desirable to subsequently confirm the result by plating out on agar an aliquot of the contents of a well within which any *Salmonella* is grown (eg a "third" well including a growth medium). To assist with sealing of the wells of the module, the wells are preferably provided with an upstanding lip upon which an adhesive-backed foil or tape may be sealingly affixed.

In a related aspect, the present invention also provides a novel machine for use with a dipstick and module of the present invention which is characterised by a reader means for reading the regions of the dipstick, said reader being arranged to move horizontally only in the machine, with the dipsticks being raised and lowered on a generally vertical axis to present the various regions of the dipstick to the reader means.

This arrangement makes the machine simpler to construct control and operate as the reader means, typically comprising a light or reflectance detector (eg a CCD or photopic sensor) and one or more light sources (eg LED(s)), only has to move in a horizontal direction.

The present invention also provides a machine which may be used with a dipstick and module of the present invention which is characterised by a reader means for reading the regions of the dipstick, said reader comprising a light or reflectance detector and one or more light sources.

The light source(s) used in the reader means preferably comprises a pair of LED's arranged so as to uniformly illuminate the dipstick in the region of the front face from where the results are to be read. Each LED may provide a light band within the range of about 20 to 40°, more preferably about 30° and may be placed at an angle to the front face of the dipstick which is in the range of about 60 to 80', more preferably about 70'.

The present invention further provides a novel machine for use with a dipstick and module of the present invention which is characterised by the dipstick being automatically and sequentially moved to and lowered into and raised from wells or tubes in the module in sequence with the dipstick remaining in each well for a predetermined period of time.

Automatic movement of the dipstick rather than say the liquids associated with the assay makes operation of the system easier and more reliable.

The machine may include a head defining a gripper means for grasping a top portion of the dipstick. The head is preferably adapted to simultaneously grasp the top portion of more than one dipstick, such that the machine may simultaneously move dipsticks between the slots and wells or tubes of respective modules so as to allow simultaneous and multiple assays to be conducted.

It is preferred that the movement of the head and hence the dipstick may controlled to suit particular assays being carried out by the machine. This is preferably achieved through the use of a smartcard and smartcard reader.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE ACCOMPANYING FIGURES

A specific embodiment of the invention as applied to the detection of a target microorganism will now be described, with reference to the accompanying figures in which:—

Figure 8B:
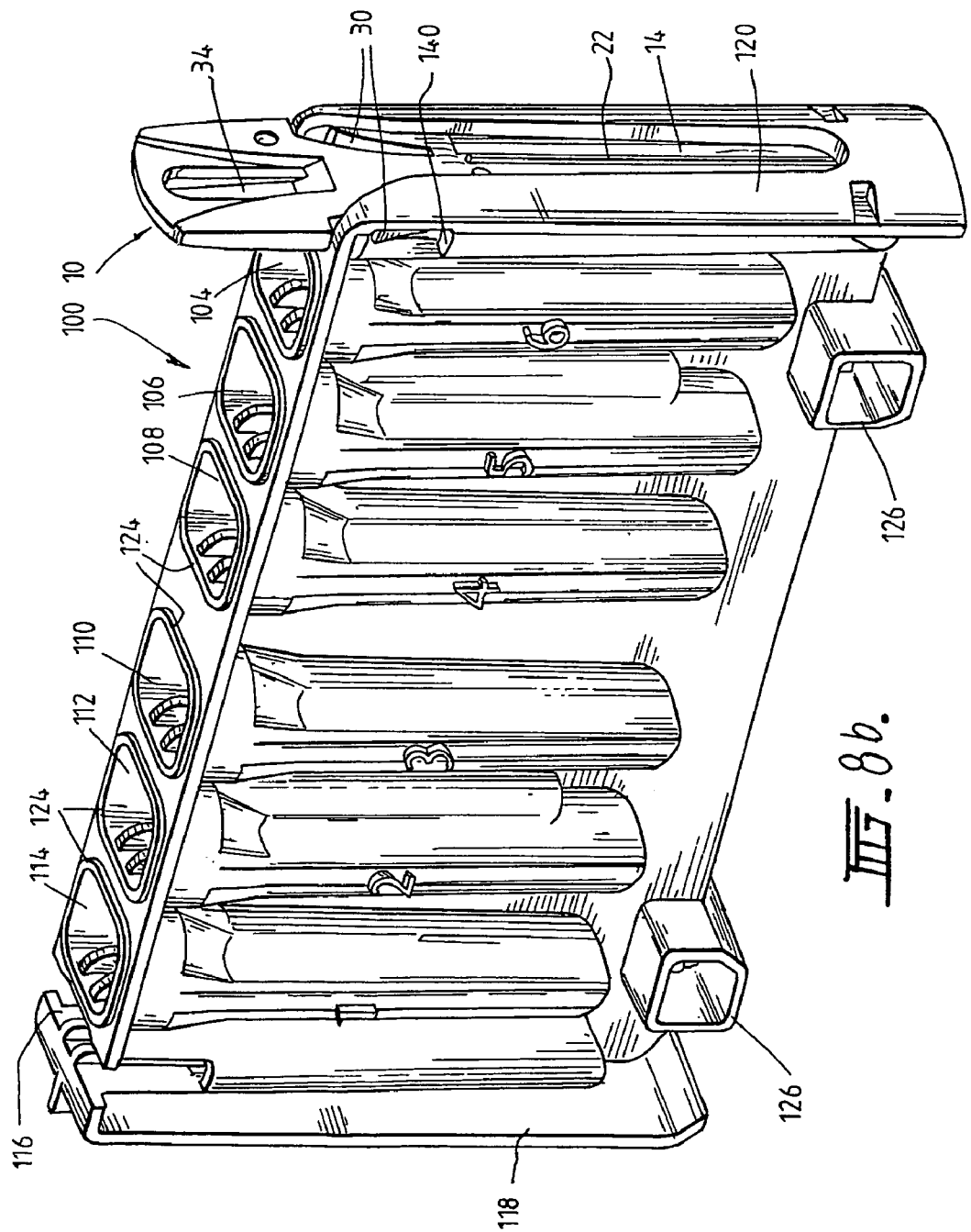
Figure 12A:
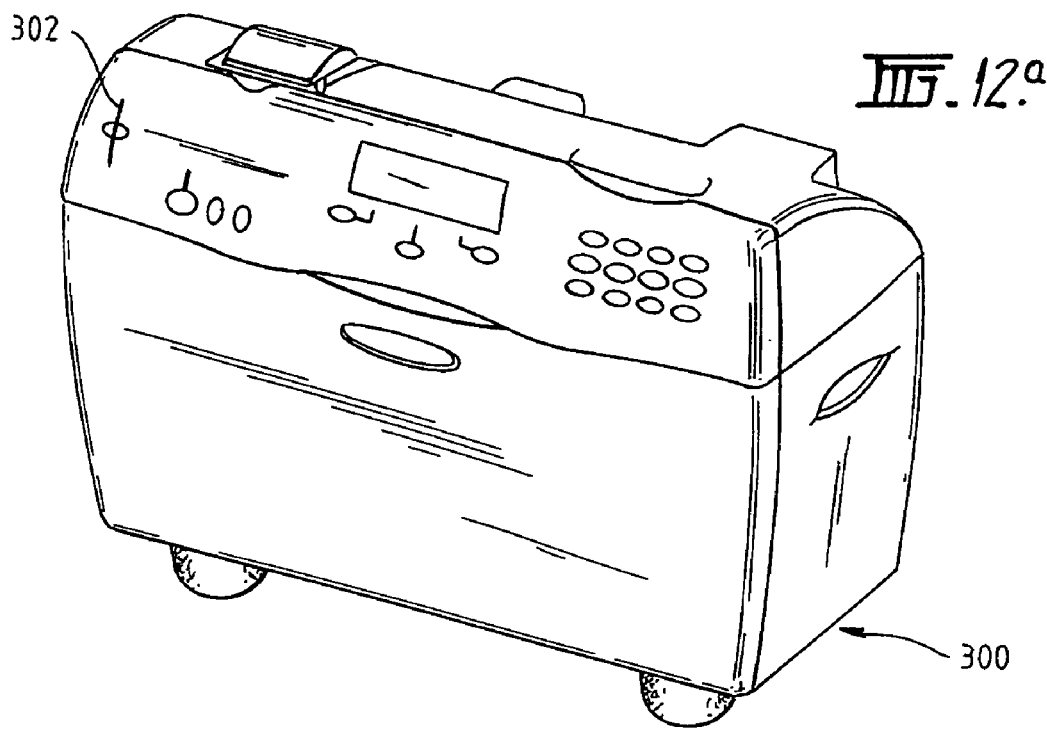
Figure 12B:
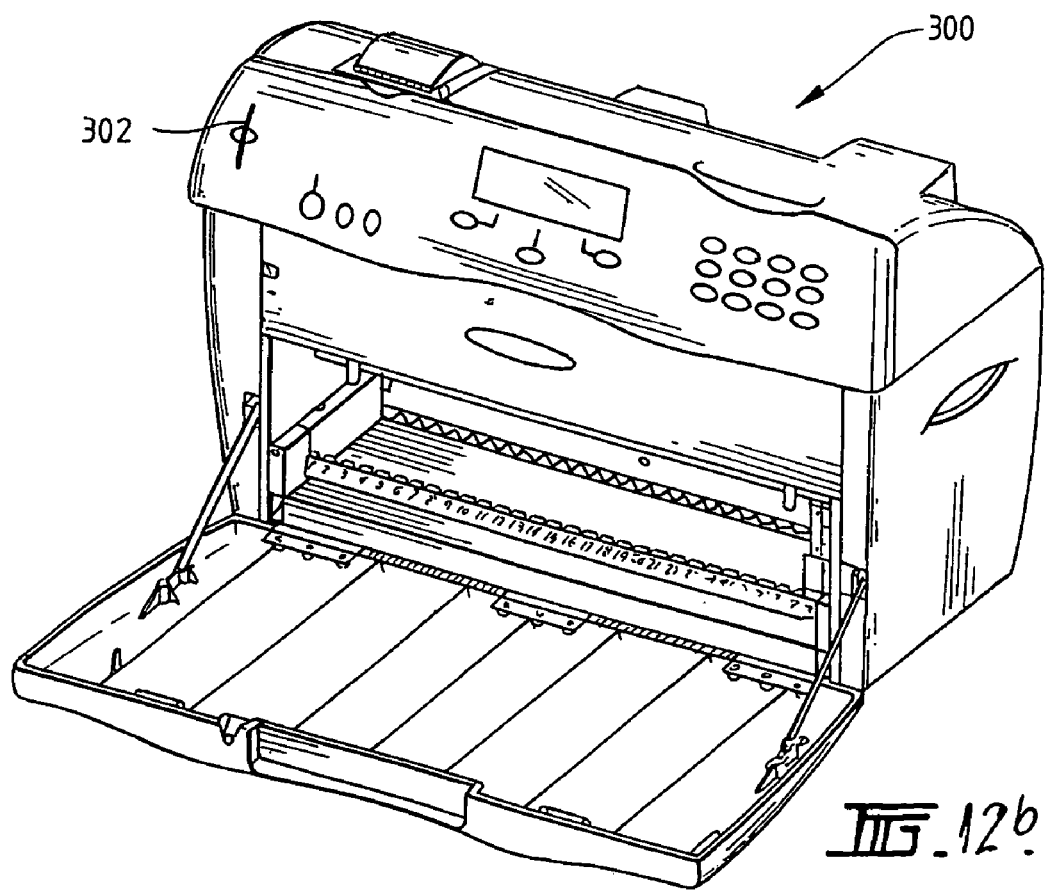

FIG. 1 is a perspective view of a dipstick embodying the present invention;

FIG. 2 is a front view of the dipstick of FIG. 1;
FIG. 3 is side view of the dipstick of FIG. 1;
FIG. 4 is a rear view of the dipstick shown in FIG. 1;
FIG. 5*a* is a top end view of the module associated with the dipstick;
FIG. 5*b* is a bottom end view of the module associated with the dipstick;
FIG. 6*a* is a side elevation of the module associated with the dipstick;
FIG. 6*b* is an opposite side elevation of the module associated with the dipstick;
FIG. 7*a* is an end elevation of one end of the module of FIGS. 5*a* and *b;*
FIG. 7*b* is an opposite end elevation of one end of the module of FIGS. 5*a* and *b;*
FIG. 8*a* is a perspective view of the module;
FIG. 8*b* is a perspective view of the dipstick inserted in a slot of the module;
FIG. 9 is a perspective view of a first part of a gripper which engages the dipstick in the automated immunoassay machine;
FIG. 10 is a perspective view of the assembled gripper comprising first and second parts;
FIG. 11 is an exploded perspective view of a "multi-gripper" comprising two metal, preferably aluminium, bars, machined to provide slots for up to 30 dipsticks, the two bars incorporating 30 springs, one for each gripper position. The two bars are screwed together to form a complete "multi-gripper" assembly.
FIG. 12*a* illustrates an automated immunoassay machine;
FIG. 12*b* illustrates an automated immunoassay machine with the front door in the open position; and
FIG. 13 schematically illustrates an optical reader of an automated immunoassay reader, and the arrangement thereof relative to a dipstick.

DETAILED DESCRIPTION OF THE INVENTION

Referring to the drawings, FIG. 1 shows a solid support in the form of a dipstick 10. The dipstick is generally elongate and planar. The dipstick is preferably made from a "general purpose" polystyrene plastic and is of a substantially uniform white colour and has a substantially uniform level of opacity. The dipstick is for insertion into wells of a module 100 illustrated in FIGS. 5 to 8 described in more detail below. The dipstick defines a lower part 14 which in use is lowered into wells or slots defined in the module and an upper part 12 which in use, is grasped by an automated immunoassay machine 300 (shown in FIGS. 12*a* and *b*) which is programmed to move the dipstick into the various wells of the module according to a programmed sequence of operations.

The lower part of the dipstick 14 has a front face 14*a* best seen in FIGS. 1 and 2 and a rear face 14*b* best seen in FIG. 4. The lower portion 14 of the dipstick is a generally rounded base 16 and sides 18 and 20 which gradually taper outwardly from the base. Two parallel elongate rails 22 extend from dose to the base 16 of the lower portion to a frangible portion 15 separating the lower portion 14 from the upper portion 12. As is best seen in FIG. 1, a series of four regions 24 are defined in the front face of the dipstick between the rails 22. The regions which in the preferred embodiment are indicated by the numbers "1", "2", "3", and "4" comprise part of the chemistry of a process for detecting microorganisms. In particular, the two uppermost regions "1" and "2" comprise the chemistry necessary for positive and negative controls. Two of the other regions "3" and "4" comprise, for example, highly specific purified antibodies (such as, monoclonal antibodies) to selectively capture a target microorganism, such as *Salmonella* or *Listeria*. One or both of the regions may be used. There is a relatively larger space between regions "3" and "4".

This specification is not specifically concerned with the chemistry of the process, rather with apparatus for carrying out the process. The skilled person can turn to Australian patent specification No. 610925, the contents of which are incorporated herein by reference, for a detailed discussion of the chemistry of the process.

The reverse side 14b of the dipstick, (best seen in FIG. 4) is also generally planar and also defines spaced apart ribs 26. In contrast with the rails 22 on the front of the dipstick, ribs 26 taper inwardly from the base 16 of the dipstick towards a frangible portion 15. The ribs 26 are also spaced apart at a greater distance relative to the rails 22. As shown in FIG. 3, the height or thickness of the ribs gradually increases from the base 16 as the ribs extend towards the upper part of the dipstick. A through hole 28 extends through the dipstick near the frangible portion 15.

A pair of outwardly curved flexible arms 30 extend away from either side of the dipstick, a gap 32 being defined between each arm of the dipstick and the dipstick itself. The arms are relatively flexible and may bend towards the central portion of the dipstick to close or partly close the gap 32.

The upper part of the dipstick 12 is configured to engage with a gripper of the machine. Two embodiments of the gripper are shown in the figures. First, a single gripper is shown in FIGS. 9 and 10, and second, a "multi-gripper" is shown in FIG. 11. As seen in FIG. 1, a flexible tongue portion 34 is defined in an elongate aperture in the upper portion 36. A hemispherical protrusion 38 is defined on a free end of the tongue 36, best seen in FIG. 4. The front face of the upper portion of the dipstick defines an outwardly expanding flared recess 39. The recess 39 and tongue 34 are used to align and secure the dipstick in the gripper.

A hole 42 is defined in the upper portion to one side of the central axis A of the dipstick. This is used to locate the dipstick during the application of the binding partner (and substances providing positive and negative controls) during manufacture of the dipstick. It is also used to provide a reference point for the reader of the machine of the invention, to assist in reading results from the dipstick.

FIGS. 5 to 8 illustrate the module 100 which is used with the dipstick. The module comprises an initial dipstick location slot 102 at one end of the module, an end slot 116 and a series of six wells 104, 106, 108, 110, 112, 114 "tubes 1 to 6" disposed in a line between the start slot and the end slot. Each of the wells are provided with an upstanding hp 124 (best seen in FIG. 8a) to allow easy sealing with an adhesive-backed foil or tape. The device is moulded in a plastic that is resistant to gamma radiation. The module may be provided with a pair of feet 126 which may reduce flex in the module (which may assist in the sealing operation(s) of the module) and be shaped to provide a "grip" for automated manufacturing processes. The shape and configuration of the module and the start and end slots and the six wells is such as to enable satisfactory automation of the process, as follows.

First, the shape of the front 118 of the module and the rear 120 of the module is different. When tests are being carried out by automation, the modules are located in side by side relation in stainless steel trays, so that the automated immunoassay machine 300 (shown in FIGS. 12a and b) can carry out a number of assays in parallel at the same time. The different configuration of the front and rear portions of the module in conjunction with the configuration of the tray, ensures that the trays can only be loaded in the tray in one direction. This is important as the process only works if the steps are carried out in the correct order.

At the end of the process, the results are read in the machine by an optical reader. Accordingly, it is important that the dipstick be correctly oriented so that it faces the correct direction at the end of the testing procedure with the regions facing the optical reader. As seen in FIGS. 5a and b, two spaced apart rails project into the interior of the initial slot 102 from the back wall of the slot These rails are spaced apart at the same distance as the rails 22 projecting from the front of the dipstick. Identical pairs of rails project into the interior of each of the wells and the end slot from their respective front walls. These rails widen tapering outwardly as they extend down into the slots/wells. This is best seen in FIGS. 7a and b, which shows the rails in the end slot 120. The width of the slot 102, measured from the front wall 102a to the rear wall 102b in the direction of the longitudinal central axis of the module, is greater than the thickness of the dipstick 10 taking into account both the front rails 22 and the tapered ribs 26. However, the width of the slot minus the width of the ribs 122 is narrower than the thickness of the thicker parts of the dipstick where the tapering ribs 26 are relatively thicker. Thus, because the rails 22 are spaced apart the same distance as the ribs 122, it is impossible to properly insert the dipstick in the module with rails 22 facing the ribs 122 of the module as the effective width of the slot is less than the thickness of the dipstick. The further the dipstick is inserted into the front slot in this orientation, the more difficult insertion becomes, the ribs 26 gradually increase in thickness. However, if the dipstick is inserted with the outwardly tapering ribs 26 facing the front of the module, those ribs, being spaced wider apart than ribs 122, locate either side of those ribs, and the dipstick can be fully inserted into the starter slot 102. Insertion is assisted since the ribs 26 taper outwardly at approximately the same angle as the ribs 122.

Each of the subsequent six wells of the module comprises a slot portion which is essentially identical to the initial slot portion, including, as discussed, the provision of the outwardly tapering ribs but includes an outwardly extending bulbous portion 130 which allows an increased volume of fluid (reagent) to be located in the well as compared with the front slot 102, whilst still providing the same protection against the dipstick being incorrectly inserted since the side portions of the wells are essentially the same width as the starter slot. The bulbous portion also allows more reagent to come into contact with the front face of the dipstick particularly when the dipstick is jiggled in the well. This is best seen in FIGS. 6a and b. The uppermost parts of the wells taper outwardly and this is to receive the outwardly extending arms 32 of the dipstick.

The end slot also defines two outwardly tapering ribs but also as shown in FIG. 7b, the rear wall of the end slot is substantially cut away to allow the dipstick to be viewed from the rear of the module when the dipstick is located in the end slot. This allows an optical reader comprising a CCD, photopic sensor or the like to be used to read the dipstick to assess the colour of the dipstick to see whether there is a positive or negative result from the test. This process, which in Australian patent specification No. 610925 is done by eye, may be automated in the machine 300.

To prevent reuse of the dipstick, and to lock the dipsticks into the module to allow separation of the machine from the dipsticks as seen in FIG. 6a, two cut out portions 140 are defined in the upper parts of the side walls of the end slot. When the dipstick is fully inserted into the end slot, the flexible arms 32 are initially compressed inwardly and then when the top 32A of each arm drops below the rim of the module, the arms 32 expand outwardly into the cut-out portions 140. Any attempt to remove the dipstick by pulling it upwardly, damages the dipstick by causing the arms to break.

The dipstick includes a frangible portion 15 to allow the upper and lower portions of the dipstick to be separated by bending or snapping. Removal of the upper portion of the dipstick when located in the end slot of the module allows for the wells to be readily sealed with an adhesive-backed foil or tape.

The gripper assembly 200 shown in FIGS. 9 and 10 comprises two discrete parts, namely a first part 201 and a second part 202. The two parts are joined by a screw (not shown) passing through hole 204, and are aligned by studs (not shown) and receiving apertures 203. A slot 205 is defined between the two parts of the gripper into which the upper portion 12 of the dipstick locates The slot is configured to mate with the top of the stick.

In particular, the flexible tongue 34 of the dipstick is received within an elongate channel 206 defined on part 201 and the flared recess 39 locates around a generally trumpet shaped formation 208 on part 201 formed between the first and second parts.

When the tongue 34 is located in the slot, the hemispherical protrusion 38 locates in a recess (not shown) in part 202 and acts to retain the tongue 34 within the slot and, as a consequence, the upper portion 12 of the dipstick remains gripped by the gripper assembly 200.

The "multi-gripper" assembly shown in FIG. 11 comprises two metal, preferably aluminium, bars 400a and 400b, machined to provide slots for up to 30 dipsticks, the two bars incorporating 30 springs (eg 401), one for each gripper position. The two bars are screwed together to form a complete "multi-gripper" assembly. The multi-gripper enables multiple dipsticks, normally up to 30, to be gripped at the same time, and moved between the slots, wells or tubes of respective modules.

An optical reader 500 is shown in FIG. 13. The optical reader comprises a pair of LED's (501 and 502) angled at about 72' to the front face 503 of the dipstick 504. For assays involving the use of alkaline phosphatase and BCIP/NBT (Bromochloroindolyl phosphate/nitroblue tetrazolium) substrate, the purple coloured positive results are best read using LED's emitting green light, preferably of about 510 to 590 nm, more preferably of about 530 to 570 nm, most preferably about 530 nm. Suitable LED's are available from Agilent (USA), Kingbright (Taiwan) and Toyoda (Japan). The pair of LED's (501 and 502) preferably provide light of an intensity of about 8 to 12 candellas incident on the front face 503 of the dipstick 504. The light band emitted by the LED's may be within the range of about 20 to 40°, more preferably about 30°. The LED's are arranged on either side of a reflectance collecting tube 505 for the photopic sensor 506. The collecting tube 505 is about 30 mm in length and has an outer diameter of about 1.6 mm and an internal diameter of about 1.2 mm. The collecting tube 505 is preferably internally etched with phosphoric acid and painted or coated with a matt black finish. The front of the collecting tube 507 is best located between about 50 and 70 mm from the front face 503 of the dipstick 504.

During the process of manufacturing of dipsticks for detection of a target microorganism, antibodies specific to the microorganism are applied to one or two of the regions 24, typically region "4" or, if needed, region "3". One of the other regions comprise substances for positive control, typically region "1", and region "2" typically comprises a negative control.

In use, the process for carrying out automated tests for *Salmonella* are as follows.

The modules and dipsticks are either warmed or allowed to reach room temperature. A stainless steel tray is removed from the automated immunoassay machine 300 placed on the bench and modules are locked into the tray. The tray defines numbered positions and the modules are placed on the tray according to the numbers on the tray as instructed by the machine. The modules are supplied containing all the necessary reagents, and washes with the wells sealed with foil to retain and protect the reagents apart from the sample itself, which is loaded into buffer in the first well of the module, after the foil covering the wells has been removed from the module. The dipstick is then inserted into the first slot at the front of each module in the correct orientation assisted by the provision of the various ribs. The tray is then placed into the automated immunoassay machine. Once the test has begun, the "multi-gripper" comprising an aluminium arm inside the machine comprising two bars defining a series of gripper slots, is moved downwards onto the dipsticks and the grippers grab the upper portions 12 of the dipsticks. The dipsticks are lifted by the arm from the starting slots and may be initially moved to the back of the machine, that is, to the end slots, where they can be read by an optical reader to establish a background signal for each dipstick.

The dipsticks are moved to "tube one", which contains the sample to be tested, for a predetermined period of time, which for the *Salmonella* test is, typically, twenty minutes. At this stage, the dipsticks may be raised and lowered inside the tubes to "jiggle" them and ensure that the contents of the tube are mixed. In the case of a *Salmonella* test, this also ensures that the buffer additive, initially located in tube one, is mixed into the sample which is added to tube one.

The arm is then raised and the dipsticks are moved out of "tube one" and lowered into "tube two" for washing in a wash solution (eg modified buffered peptone water; MBPW) and are washed by moving the dipsticks up and down.

The arm is then raised and the dipsticks are lifted out of tube two and loaded into tube three which contains a growth medium (eg in the case of *Salmonella*, this may be M broth). The dipsticks remain in tube typically for three to four hours during which the temperature within the tube two is raised to an appropriate culture temperature by a heater unit (eg a flexible heating mat) within the automated immunoassay machine 300. Occasional jiggling of the dipsticks may be carried out.

The arm is then raised again and the dipsticks are lifted out of tube three and lowered into tube four which contains an enzyme-linked antibody conjugate. Typically, the dipsticks remain here for thirty minutes. The arm is then raised and the dipsticks are lifted out of tube four and lowered into tube five which contains a wash solution. The dipsticks are washed for ten minutes with the arms continuously raising and lowering the dipsticks to ensure that the dipsticks are properly washed.

The arm is then raised, lifting the dipsticks out of tube five, and the dipsticks are then lowered into tube six which contains about 1 ml of substrate for the enzyme. For *Salmonella*, the dipstick will remain in this tube for about ten minutes.

The arm is then raised and the dipsticks are lifted out of tube six, re-aligned by moving back to the starting slot 102 and then inserted into the end slot 116 (ie the "reading slot") of the module. The optical reader then moves into line with the dipstick to read the dipstick in the first module. The dipstick is moved so that the reader detects the home position defined by the hole 28. The dipstick is then raised so that the optical reader can read the negative control area, the positive control area and the test area. The optical reader then moves until it is level with the dipstick associated with the second module and performs the same process and so on with the third module until all the dipsticks are read. It is important to note that because the dipsticks can move up and down in a vertical direction, the optical reader only needs to be able to move along a horizontal axis. The arm is then lowered so that the dipsticks are pushed as far down into the tray as they can go which drops the curved arms 32 into the modules (and also inhibits reuse of the dipsticks).

The arm is then raised and the dipsticks which are now locked into the modules separate from the multi-gripper.

Difficulties in the optical reader correctly reading results may be experienced if the dipstick is not placed in the end slots such that the front face 14a of the dipstick is not substantially vertical (ie such that region "4" of the dipstick may be relatively doser or further away from the optical reader than region "1"). To overcome such a difficulty, the background reading scan may be used to establish a baseline between readings either side of each of regions "1", "2", "3" and "4", and the result readings may be subjected to an algorithm that calculates:

(i) For the positive control (PC) region (typically region "1"), the maximum or total decrease in reflectance from the PC baseline;

(ii) For the negative control (NC) region (typically region "2"), the maximum increase in reflectance from the NC baseline; and (ii) For the sample (S) region (typically region "4"), the maximum or total decrease in reflectance from the S baseline.

For other microorganisms such as *Listeria*, the tests are run slightly differently with different timing and different reagents. Accordingly, the machine may have a smartcard reader 302, for receiving smartcards particular to certain microorganisms or for specific assay protocols, for example testing for *Salmonella* in confectionary involves a different protocol to testing for *Salmonella* in a different type of food product. The smartcards program the machine to perform the test in the manner appropriate for the particular microorganism.

The system is not limited to testing for bacteria such as *Listeria* and *Salmonella*. Any microorganism which is capable of in vitro growth including yeasts, moulds, protozoa (eg *Cryptosporidium*) and other bacteria (eg *Escherichia coli, Legionella, Campylobacter, Staphylococcus, Bacillus* and *Pseudomonas*), can be tested for. The binding partner for capture of such microorganisms is preferably selected from antibodies or antibody fragments (eg Fab and scFv fragments) which specifically bind to an antigenic determinant or hapten on the surface of the particular target microorganism, for example an antigenic determinant present in a cell wall protein such as a porin or in a flagellar protein. For detection of a captured target microorganism, typically an enzyme-linked antibody conjugate is used which specifically binds to any antigenic determinant or hapten present in a cell wall protein such as those mentioned above or, otherwise, in a secreted protein such as a toxin (eg enterotoxins of *Bacillus* and *Staphylococcus*, and emetic toxins of *Bacillus*).

The system can also be used to capture and detect other agents that may not require a growth step to enable detection. Such other agents include viruses (eg HIV, HCV, etc), prions (eg BSE), toxins (eg enterotoxins of *Bacillus* and *Staphylococcus*, and emetic toxins of *Bacillus*), and other analytes including antibodies, antigens (eg food allergens such as milk proteins including caseins, and peanut proteins), nucleic acids, chemical residues (eg antibiotic and pesticide residues), microbial metabolites (eg mycotoxins and phycotoxins), and vitamins.

The system can also be operated manually. In such cases, the modules may be held in a plastic tray, with the dipsticks being moved between the slots and wells of the module by hand, and the modules being moved in and out of an incubator as required. The results may be read by eye and comparison against a standard colour chart.

EXAMPLE 1

Analysis of *Salmonella* Using a *Salmonella* Assay Dipstick and Module

Materials and Methods

Gamma-irradiated white polystyrene plastic dipsticks as shown in FIG. 1, were prepared by coating an antigen solution (ie 10 µl protein extracts of *Salmonella* bacteria) onto region 1 (ie to provide a positive control), and a capture antibody solution (ie 10 µl affinity-purified antibody recognising *Salmonella*) onto regions 3 and 4 (ie for sample binding). These solutions were prepared in buffer using standard procedures. The solutions were air-dried, and then the dipsticks were incubated in a solution of a protein blocking agent (eg casein or albumin) in buffer. The dipsticks were then air-dried again and sealed with a dessicant sachet in a foil pouch for storage at 4C prior to use.

Assay modules having a configuration as shown in FIGS. 5-7, and which were suitable for enriching for and assaying for *Salmonella* were prepared substantially in the manner described in Australian patent specification No. 610925. Tubes 1 to 6 were filled as follows:

Tube 1: 0.75 ml sample additive (as per Tecra® *Salmonella* Unique™ assay protocol)

Tube 2: peptone-buffered water wash solution (1.5 ml) (MBPW)

Tube 3: enrichment broth for the enrichment of *Salmonella* (1 ml)

Tube 4: enzyme-linked antibody conjugate (ie which recognises *Salmonella* bacteria) in buffer solution (1 ml)

Tube 5: wash solution (1.5 ml)

Tube 6: substrate solution (ie BCIP/NBT) for the enzyme of the enzyme-linked antibody conjugate of tube 4 (1 ml)

The tubes were sealed with an aluminium foil seal.

For analysis of *Salmonella* in various food matrices, 10 g samples were taken and mixed with 90 ml sterile modified peptone buffered water (MBPW), and pre-warmed to room temperature. Each sample was then mixed and sealed for incubation at 35-37° C. for 16-20 hrs (Pre-enrichment step). Additional samples were prepared by spiking *Salmonella* species directly into the food. Spikes were prepared at a level of 10 cells per food sample. The spiked food samples were chilled before extraction with MBPW.

The aluminium foil seal on each assay module was removed, and a 1 ml sample from a pre-enrichment sample was each transferred to the tubes 1 and a dipstick inserted into each of the launch slots. Each module was placed in a tray which was then inserted into the immunoassay machine shown in FIG. 12 and the machine programmed with a *Salmonella* assay smartcard. The programmed assay involved:

(i) Moving the dipsticks to tubes 1 for 20 minutes (42° C.) to capture any *Salmonella* present with the capturing antibody.

(ii) Moving the dipsticks to tubes 2 for 7 minutes (42° C.), with jiggling, for a first wash to remove unbound material.

(iii) Moving the dipsticks to tubes 3 for 4 hours (42° C.), to allow the captured bacteria to grow (enrichment step).

(iv) Moving the dipsticks to tubes 4 for 30 minutes (room temperature) to allow specific binding of the detection antibody (ie the enzyme-linked antibody conjugate).

(v) Moving the dipsticks to tubes 5 for 10 minutes (room temperature), with jiggling to wash to remove unbound material.

(vi) Moving the dipsticks to tubes 6 for 10 minutes (room temperature) to allow development of purple coloured results.

(vii) Moving the dipsticks to the end slots for reading of the results.

The machine was activated and run for a total assay time of 5 hr 45 min. At the end of this period, the sample results were printed or downloaded to a computer. The tray containing the modules was then removed and the dipsticks examined visually to confirm the results. Samples taken from the tubes 3 were streaked onto XLD and HE plates (Oxoid Unipath, United Kingdom) to confirm the presence of *Salmonella* in positive samples, using conventional procedures.

Results

The results are shown in Table 1.

EXAMPLE 2

Analysis of *Listeria*

Materials and Methods

Gamma-irradiated white polystyrene plastic dipsticks as shown in FIG. 1, were prepared by coating an antigen solution (ie 10 μl protein extracts of *Listeria* bacteria) onto region 1 (ie to provide a positive control), and a capture antibody solution (ie 10 μl affinity-purified antibody recognising *Listeria*) onto regions 3 and 4 (ie for sample binding). These solutions were prepared in buffer using standard procedures. The solutions were air-dried, and then the dipsticks were incubated in a solution of a protein blocking agent in buffer. The dipsticks were then air-dried again and sealed along with a dessicant sachet in a foil pouch for storage at 4C prior to use.

Assay modules having a configuration as shown in FIGS. 5-7, and which were suitable for enriching for and assaying for *Listeria* were prepared substantially in the manner described in Australian patent specification No. 610925. Tubes 1 to 6 were filled as follows:

Tube 1: no solution.

Tube 2: no solution (this tube is not used in the *Listeria* assay)

Tube 3: enrichment broth for the growth of *Listeria* (1 ml)

Tube 4: enzyme-linked antibody conjugate (ie which recognises *Listeria* bacteria), in buffer solution (1 ml)

Tube 5: wash solution (1.5 ml)

Tube 6: substrate solution (BCIP/NBT) (1 ml)

The tubes were sealed with an aluminium foil seal.

Analysis of *Listeria* was conducted in a similar manner to that employed for *Salmonella* in Example 1.

TABLE 1

| | | | | | Confirmation of result | | | |
|---|---|---|---|---|---|---|---|---|
| Unique Plus Instrument Sample and Result | | | | Stick | Enrichment confirmation | | Tube 3 confirmation | |
| Sample | Bacteria | Spike | Result | Visual | XLD | HE | XLD | HE |
| Sultanas | nil | 0 | −ve | −ve | No growth | No growth | No growth | No growth |
| | *S. dublin* | 10 | + | + | Typical | Typical | Typical | Typical |
| | *S. dublin* | 10 | + | + | Typical | Typical | Typical | Typical |
| Brazil Nuts | nil | 0 | −ve | −ve | No growth | No growth | No growth | No growth |
| | *S. bredeney* | 10 | + | + | Typical | Typical | Typical | Typical |
| | *S. bredeney* | 10 | + | + | Typical | Typical | Typical | Typical |
| Roasted Peanuts | nil | 0 | −ve | −ve | No growth | No growth | No growth | No growth |
| | *S. bredeney* | 10 | + | + | Typical | Typical | Typical | Typical |
| | *S. bredeney* | 10 | + | + | Typical | Typical | Typical | Typical |
| Cherries | nil | 0 | −ve | −ve | No growth | No growth | No growth | No growth |
| | *S. montevideo* | 10 | + | + | Typical | Typical | Typical | Typical |
| | *S. montevideo* | 10 | + | + | Typical | Typical | Typical | Typical |
| Raspberries | nil | 0 | −ve | −ve | No growth | No growth | No growth | No growth |
| | *S. dublin* | 10 | + | + | Typical | Typical | Typical | Typical |
| | *S. dublin* | 10 | + | + | Typical | Typical | Typical | Typical |

Cultures of *Listeria* were prepared containing 10⁶ cells/ml and a 1 ml sample of each culture introduced to tube 1 of a module from which the foil seal had been removed. Dipsticks were then inserted into the launch positions of each module, and each module inserted into an assay tray. Additional samples were prepared and their modules inserted into the tray alongside. The tray containing the modules was inserted into the immunoassay machine which had been programmed with a smartcard for operation of a *Listeria* assay protocol. The protocol did not involve dipping the dipsticks into the tubes 2. The programmed assay involved:

(i) Moving the dipsticks to tubes 1 for 1 hour (31° C.) to capture any *Listeria* present with the capturing antibody.

(ii) Moving the dipsticks to tubes 3 for 5 minutes (31° C.), to allow the captured bacteria to grow.

(iv) Moving the dipsticks to tubes 4 for 30 minutes (42° C.) to allow specific binding of the detection antibody (ie the enzyme-linked antibody conjugate).

(v) Moving the dipsticks to tubes 5 for 10 minutes (room temperature), with jiggling to wash to remove unbound material.

(vi) Moving the dipsticks to tubes 6 for 15 minutes (room temperature) to allow development of purple coloured results.

(vii) Moving the dipsticks to the end slots for reading of the results.

The machinne indicated a total assay time of 7 hours, and at the end of this period, the sample results were printed. The tray containing the modules was then removed and the dipsticks examined visually to confirm the results.

Results

The results are show in Table 2.

TABLE 2

| Dipstick | Name | Result |
|---|---|---|
| 1 | *L. monocytogenes* | Positive |
| 2 | *L. monocytogenes* | Positive |
| 3 | *L. innocua* 6A | Positive |
| 4 | *L. innocua* 6B | Positive |
| 5 | *L. innocua* | Positive |
| 6 | *L. innocua* | Positive |
| 7 | *L. innocua* | Positive |
| 8 | *L. innocua* | Positive |
| 9 | *L. innocua* | Positive |
| 10 | *L. innocua* | NC Error |
| 11 | *L. innocua* | Positive |
| 12 | *L. innocna* | Positive |
| 13 | *L. innocua* | Positive |
| 14 | *L. seeligeri* | Positive |
| 15 | *L. seeligeri* | Negative |
| 16 | *L. seeligeri* | Negative |
| 17 | *L. seeligeri* | NC Error |
| 18 | *L. seeligeri* | Positive |
| 19 | *L. welshimeri* 4 | Positive |
| 20 | *L. welshimeri* 4 | Positive |

*NC error is reported by the assay when the dipstick is unreadable for any reason. (Dipstick 10, this was repeated at a later date).

Example 3

Analysis of *Staphylococcal* Enterotoxins

Materials and Methods

Gamma-irradiated white polystyrene plastic dipsticks as shown in FIG. 1, were prepared by coating an antigen solution (ie 10 μl enterotoxin protein) onto region 1 (ie to provide a positive control), and an antibody solution (ie 10 μl of affinity-purified capture antibody recognizing *S. aureus* enterotoxin) onto regions 3 and 4 (ie for sample binding). These solutions were prepared in buffer using standard procedures. The solutions were air-dried, and then the dipsticks were incubated in a solution of a protein blocking agent in buffer. The dipsticks were then air-dried again and then sealed along with a dessicant sachet in a foil pouch for storage at 4° C. prior to use.

Assay modules suitable for *S. aureus* enterotoxin detection were prepared. Tubes 1 to 6 were filled as follows:

Tube 1: no solution

Tube 2: wash solution (1.5 ml)

Tube 3: wash solution (1.5 ml)

Tube 4: enzyme-linked antibody conjugate (ie which recognises *S. aureus* enterotoxin) in buffer solution (1 ml)

Tube 5: wash solution (1.5 ml)

Tube 6: substrate solution (BCIP/NBT) (1 ml)

The tubes were sealed with an aluminium foil seal.

Samples were extracted from food by mixing 10 g of food with 25-50 ml buffer using the methodology described in the Tecra® Visual Immunoassay (VIA™) kit instruction book (Tecra International Pty Ltd, Frenchs Forest, New South Wales, Australia).

An aliquot of each sample (1 ml) is introduced into tube 1 of each module together with a sample additive (as detailed in the VIA™ kit instructions) and the dipsticks inserted into the launch positions. The modules were then placed into an assay tray for loading into an immunoassay machine. The immunoassay machine was programmed with a smartcard for operation of an enterotoxin analysis assay. The programmed assay involved:

(i) Moving the dipsticks to tubes 1 for 2 hours (35-37° C.) to capture any enterotoxin present with the capturing antibody.

(ii) Moving with the dipsticks to tubes 2 for 2 minutes (28-30° C.), with jiggling, for a first wash to remove unbound material.

(iii) Moving the dipsticks to tubes 3 for 2 minutes (28-30° C.), with jiggling, for a further wash.

(iv) Moving the dipsticks to tubes 4 for 1 hour (28-30° C.) to allow specific binding of the detection antibody.

(v) Moving the dipsticks to tubes 5 for 5 minutes (2830° C.) to wash to remove unbound material.

(vi) Moving the dipsticks to tubes 6 for 10 minutes (room temperature) to allow development of purple coloured results.

(vii) Moving the dipsticks to the end slots for reading of the results.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A solid support for use in a process for the detection of an analyte the solid support comprises:

a front face and a rear face;

a binding partner specific for the target analyte adhered to the front face of the solid support either directly or indirectly through a linker, the binding partner being capable of selective capture and immobilization of the analyte;

means for protecting the binding partner from being dislodged or scraped off the solid support by physical force; said means for protecting comprising at least one rail raised from the front face and extending generally parallel to the longitudinal axis;

a lower portion for insertion into a well, tube or the like, and an upper handle portion to be grasped for moving the solid support.

2. The solid support of claim 1, wherein the solid support is in the form of a dipstick having a generally elongated and planar shaped defining a longitudinal axis.

3. The solid support of claim 2 further comprising an array of regions spaced apart along the longitudinal axis of the front face adjacent to said rail.

4. The solid support of claim 2, wherein said means for protecting comprises a pair of rails raised from the front face and extending generally parallel to the longitudinal axis, and between said pair of rails, the front face comprises an array of regions spaced apart along the longitudinal axis.

5. The solid support of claim 3, wherein said array of regions comprises 3 or 4 regions, at least one of which has said binding partner adhered thereto either directly or indirectly through a linker.

6. The solid support of claim 3 further comprising a pair of ribs disposed on the rear face and extend in a direction generally parallel to the longitudinal axis from the base of the solid support to the top of the solid support and protrude from the rear face.

7. The solid support of claim 6, wherein each of the ribs of said pair of ribs increases in height relative to the rear face as they extend towards the top of the solid support.

8. The solid support of claim 1 further comprising two flexible outwardly extending arms projecting from the opposite sides of an upper part of the lower portion of the solid support.

9. The solid support of claim 1 further comprising a frangible portion to allow the upper portion of the solid support to be snapped off.

10. The solid of claim 1, wherein the solid support is polystyrene and has a substantially uniform white color and a substantially uniform level of opacity.

11. The solid support of claim 1, wherein the binding partner is selected from the group consisting of antibodies and antibody fragments, receptor molecules, antigens or antigenic determinants, and nucleic acids.

12. The solid support of claim 1, wherein the analyte is a microorganism and the binding partner is an antibody that specifically binds to, capture and immobilize the microorganism without compromising the ability of the microorganism to replicate.

* * * * *

UNITED STATES PATENT AND TRADEMARK OFFICE
CERTIFICATE OF CORRECTION

| | |
|---|---|
| PATENT NO. | : 7,374,951 B2 |
| APPLICATION NO. | : 10/492188 |
| DATED | : May 20, 2008 |
| INVENTOR(S) | : Ash et al. |

It is certified that error appears in the above-identified patent and that said Letters Patent is hereby corrected as shown below:

Column 2,
Line 49, delete "agent" and insert in place thereof --agent,--.

Column 5,
Line 32, delete "80'," and insert in place thereof --80°,--.
Line 32, delete "70'." and insert in place thereof --70°.--.

Column 6,
Line 59, delete "dose" and insert in place thereof --close--.

Column 7,
Lines 2-3, delete "monodonal" and insert in place thereof --monoclonal--.
Line 27, delete both instances of "dose" and insert in both places thereof --close--.
Line 51, delete "hp" and insert in place thereof --lip--.

Column 8,
Line 12, delete "slot" and insert in place thereof --slot.--. (second occurrence)

Column 9,
Line 44, delete "72'" and insert in place thereof --70°--.

Column 11,
Line 23, delete "doser" and insert in place thereof --closer--.
Line 36, delete "(ii)" and insert in place thereof --(iii)--.

Column 15,
Line 7, a new paragraph should be inserted encompassing the language of lines 7-11
starting after the word "alongside." to the word "involved:".

Signed and Sealed this
Twenty-second Day of November, 2011

David J. Kappos
*Director of the United States Patent and Trademark Office*

CERTIFICATE OF CORRECTION (continued)

U.S. Pat. No. 7,374,951 B2

Column 15,
Line 27, delete "machinne" and insert in place thereof --machine--.
Line 47 (in Table 2 Dipstick 12) delete "innocna" and insert in place thereof --innocua--.

Column 16,
Line 43, delete "(2830°" and insert in place thereof --(28-30°--.
Line 58, delete "analyte" and insert in place thereof --analyte,--.